United States Patent [19]

Moretti et al.

[11] Patent Number: 4,525,466

[45] Date of Patent: Jun. 25, 1985

[54] PROCESS FOR SYNTHETIZING ZEOLITES HAVING A MORDENITE STRUCTURE AND HAVING HIGH CATALYTIC ACTIVITY

[75] Inventors: Enrico Moretti; Valentino Zamboni, both of Milan, Italy; Raymond Le Van Mao, Montreal, Canada; Mario Padovan; Marcello Solari, both of Milan, Italy

[73] Assignee: Montedison S.p.A., Milan, Italy

[21] Appl. No.: 444,355

[22] Filed: Nov. 24, 1982

[30] Foreign Application Priority Data

Nov. 27, 1981 [IT] Italy ................................ 25320 A/81

[51] Int. Cl.³ ............................................. B01J 29/18
[52] U.S. Cl. ...................................... 502/63; 502/62; 502/68; 423/328
[58] Field of Search ............................ 502/62, 68, 78; 423/328

[56] References Cited

U.S. PATENT DOCUMENTS 4,052,472 10/1977 Givens et al. ........................ 585/469
4,390,457 6/1983 Klotz ............................... 423/328 X Primary Examiner—Carl F. Dees

[57] ABSTRACT

Figure 1:
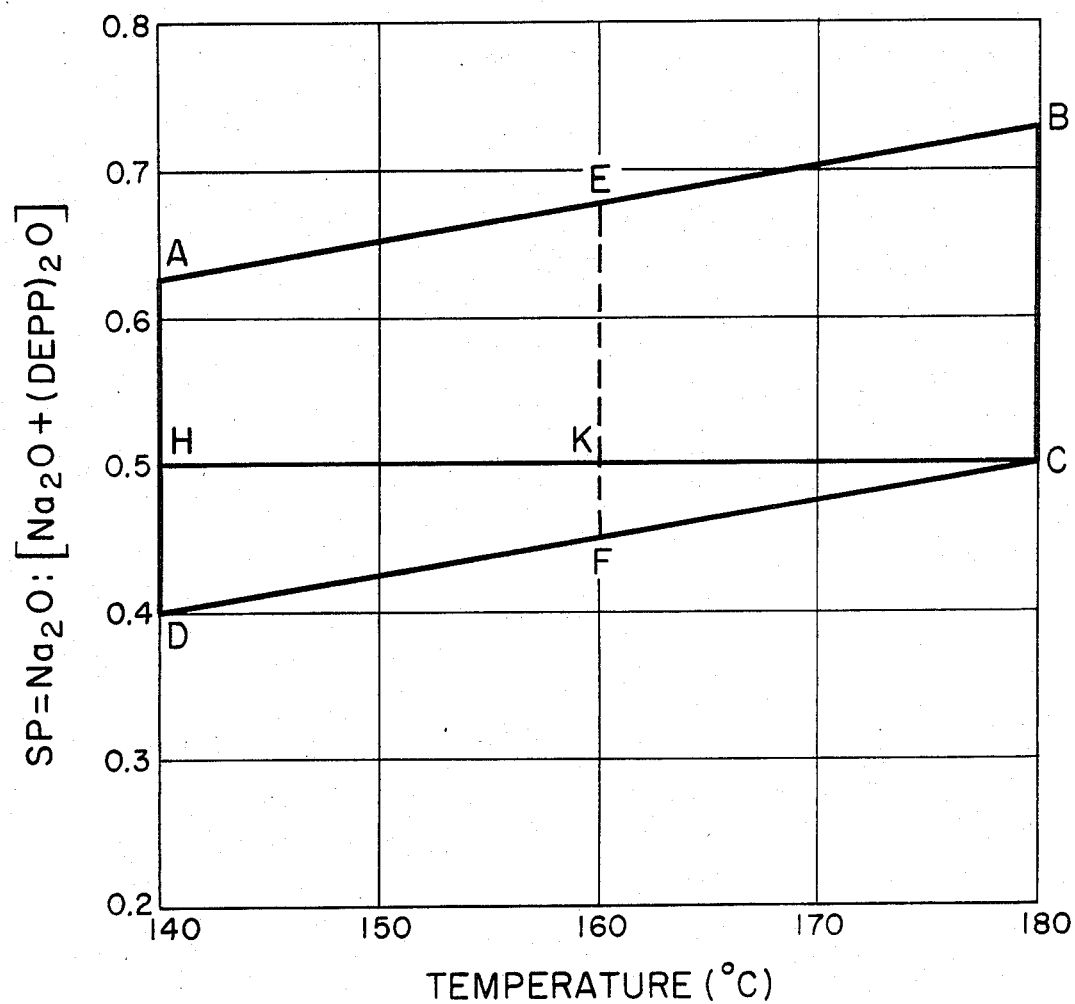

A process for synthetizing mordenites having a high catalytic activity, in which the $SiO_2:Al_2O_3$ molar ratio ranges from 16 to 40, said process comprising the step of mixing an organic base with $H_2O$ and with at least a Na compound, an Al compound, and a Si compound, wherein said base is a diethyl-piperidinium compound and wherein the crystallization temperature of mordenite and the SP factor are selected within area A B C D of FIG. 1, the crystallization time being longer than two days.

8 Claims, 3 Drawing Figures

PROCESS FOR SYNTHETIZING ZEOLITES HAVING A MORDENITE STRUCTURE AND HAVING HIGH CATALYTIC ACTIVITY

BACKGROUND OF THE INVENTION

The invention relates to a process for synthetizing zeolites having a mordenite structure and a high catalytic activity, in which the molar ratio of $SiO_2$ to $Al_2O_3$ is equal to at least 16; this kind of zeolites is referred to hereinafter as ME zeolites, ME mordenites or also as ME mordenitic zeolites.

It is known to introduce into the tridimensional structure of the zeolites, in the course of the synthesis step, an organic cation, for example a quaternary ammonium cation, such as tetrapropyl-ammonium, tetrabutyl-ammonium or diethyl-piperidinium, and it is known that these cations lead to the obtainment of particular original structures; see, for example, European patent publication 21,445, in the name of the Applicant. The inorganic cations are easily exchangeable, either totally or partially, with other cations, while the organic cations originally present are not susceptible of any further cationic exchange due to the reduce dimensions of their pores; zeolite, once it has been dehydrated, exhibits absorption characteristics.

Out of the zeolites having a pentasilicate-ring structure, a known class is the one of mordenites; they exist in nature (mordenite small ports), but are also prepared by synthesis (mordenite large ports) and the preparation thereof is known for example from R. M. Barrer "Molecular Sieves" page 39 Soc. Chem. Ind. (1968). According to U.S. Pat. No. 3,436,174, a mixture containing an Al source (e.g. Na aluminate), a Si source (e.g. Na silicate) and an alkali metal source (e.g. soda or just the silicate or aluminate) is put into $H_2O$, in defined proportions and at a suitably adjusted pH. The mixture is hydrothermally treated (with or without pressure) for a time and at a temperature such as to promote crystallization, the resulting mordenite having a general formula, for example, of the type:

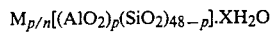

$$M_{p/n}[(AlO_2)_p(SiO_2)_{48-p}] \cdot XH_2O$$

wherein M is a cation and n the valence thereof and where p is usually such, that the molar ratio of $SiO_2$ to $Al_2O_3$ ranges from 8 to 10.

By increasing the $SiO_2:Al_2O_3$ ratio in the starting gel, besides obtaining mordenite with a final ratio of $SiO_2$ to $Al_2O_3$ equal to 10, other silicates of the type of analcite and α-quartz crystallize (R. M. Barrer et al., J. Chem. Soc. 1952, page 1561; P. K. Baipai et al., Ind. Eng. Chem. P.R.D. Vol. 17, pages 223, 1978).

The conditions for synthetizing a mordenite having a high $SiO_2/Al_2O_3$ ratio as a single crystalline phase are very critical and depend (besides on the organic base selected) on the temperature, the pH and the type of alkalinity existing, these structures being the result of complex nucleation, crystallization and recrystallization reactions in systems far from the equilibrium; see A. Erdem and L. B. Sand J. Catalysis, Vol. 60, page 241 (1978); in general, crystalline multiphase systems are obtained.

The substitution of a part of the inorganic base by a strong organic base renders the forming of crystalline $SiO_2$ less easy, at least in the range of the claimed temperatures and compositions, thus allowing the nucleation of mordenite crystals also at $SiO_2/Al_2O_3$ ratios higher than 10. In these conditions and with specific organic bases, closely related structures may form; that is the case of ZSM-5, ZSM-11 and ZSM-8 zeolites, characterized by silicate subunits similar to the ones of mordenite.

By introducing particular organic components into the crystallization mixture, mordenites having a $SiO_2/Al_2O_3$ ratio of from 15 to 30 have been produced by direct synthesis, and tetraethyl-ammonium salts (U.S. Pat. No. 4,052,472) or derivatives of neopentylamine (EP 14023) have been employed; the mordenites prepared according to this method reveal, under the electron microscope, a characteristic morphological aspect (EP 14544).

OBJECT OF THE INVENTION

It is an object of the present invention to define a method of preparing zeolites having a mordenite structure and a high silicon content and endowed with a high catalytic activity.

Further objects will be apparent from the following description.

GENERAL DISCLOSURE

In its most general form, the invention relates to a process for synthetizing mordenites having a high catalytic activity, in which the $SiO_2:Al_2O_3$ molar ratio ranges from 16 to 40, said process comprising the step of admixing an organic base with $H_2O$ and with at least a Na compound, an Al compound, and a Si compound, and being characterized in that said organic base is diethyl-piperidinium hydroxide, or a salt thereof, that crystallization temperature and factor SP (see below) are selected within area A B C D of FIG. 1, the crystallization time exceeding 2 days and preferably ranging from 4 to 7 days, and that the following molar ratios between the above-cited compounds (expressed as oxides) are employed:

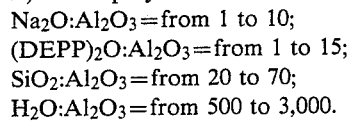

$Na_2O:Al_2O_3$ = from 1 to 10;
$(DEPP)_2O:Al_2O_3$ = from 1 to 15;
$SiO_2:Al_2O_3$ = from 20 to 70;
$H_2O:Al_2O_3$ = from 500 to 3,000.

PREFERRED EMBODIMENTS AND DETAILS

Advantageously, said ratios are in the following ranges:

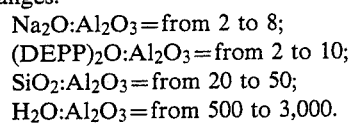

$Na_2O:Al_2O_3$ = from 2 to 8;
$(DEPP)_2O:Al_2O_3$ = from 2 to 10;
$SiO_2:Al_2O_3$ = from 20 to 50;
$H_2O:Al_2O_3$ = from 500 to 3,000.

Furthermore it is preferable when the silica dilution, i.e. the $H_2O:SiO_2$ molar ratio, ranges from 25 to 45 and preferably from 35 to 45, when said factor SP and said temperature are selected within area E B C F of FIG. 1 and when the crystallization time ranges from 4 to 6 days, factor SP being given by the expression:

$$SP = Na_2O:[Na_2O + (DEPP)_2O]$$

and meaning the molar fraction of sodium with respect to the total of the cations; diethyl-piperidinium ion is the cation:

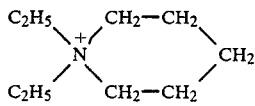

For times exceeding 7 days, surface A B C D of FIG. 1 must be shifted upwardly; instead of a Na compound it is possible to use a K compound or mixtures of compounds of Na and of K; instead of the Al compound it is possible to use a gallium compound, and instead of the Si compound, a germanium compound is employable. Crystallization can be accomplished under an autogenous pressure, in a stirrer-equipped autoclave; at the conclusion of the synthesis, the solid product is separated from the liquid product, then it is washed with $H_2O$ or with an acid solution between 15° and 95° C., until disappearance of the $Na^+$ ions from the washing liquid, and successively dried in an oven at 120° C. for 10–12 hours. After activation in air for 2–10 hours between 400° and 600° C., preferably at 540° C., the zeolite can be subjected to the exchange of cation $Na^+$ with the proton or with the ammonium ions as such or substituted by alkyl radicals; the acid form of zeolite can be obtained by exchange with the ammonium ion utilizing, for example, ammonium chloride, nitrate or hydroxide) and calcination of zeolite at from 300° C. to 650° C., preferably from 400° to 550° C. Calcination causes the ammonium ion to decompose, leaving the structure in the acid form; the ions $Na^+$ of zeolite may be also exchanged with all the cations having sizes suited to enter the channels, and in particular with the cations of the metals of Group VIII.

USE AND ADVANTAGES OF THE ZEOLITES ACCORDING TO THE INVENTION

The present invention relates furthermore to the use of ME zeolites, either or not formed, for the conversion of hydrocarbons by acid-catalyzed reactions, such as cracking, hydrocracking, reforming, aromatizations, dimerizations, polymerizations, alkylations, disproportionings, isomerizations, dealkylations, transpositions, esterifications and dehydrations.

As the $SiO_2/Al_2O_3$ ratio in mordenite increases, the catalytic activity increases expenentially, thus reaching values remarkably higher than those of other catalyst systems and in particular of the conventional mordenites as such or dealuminated and of ME-28 and ZSM zeolites, which are known due to their already high activity. ME mordenites are particularly effective towards the disproportionation of toluene to benzene and to xylenes (even at very low temperatures), said disproportioning being obtainable in a vapor phase, in the presence of hydrogen, with a molar ratio of $H_2$ to toluene ranging from 3 to 10, at temperatures from 250° to 400° C. and preferably from 300° to 350° C., at pressures from 30 to 40 atm. and at space velocities (LHSV), referred to the active component, between 1 and 5 $h^{-1}$.

Analogously, isomerization of meta-xylene, optionally in admixture with ethylbenzene and with minor amounts of the desired products (ortho- and para-xylene), can be achieved in the vapor phase, in the presence of $H_2$ (molar ratio of $H_2$ to hydrocarbon: from 3 to 10), between 200° and 350° C. and preferably between 250° and 320° C., from 10 to 20 atm. and at space velocities, referred to the active component, between 1 to 15 volumes of liquid hydrocarbon per volume of catalyst and per hour (LHSV=from 1 to 15 $h^{-1}$). ME zeolites can be used in the acid form or partially exchanged; furthermore it is possible to add active components according to techniques other than the ion exchange, such as e.g. impregnation (either in dry or in wet conditions), soaking, co-precipitation and mechanical mixing. ME mordenites can be used in various forms, for example granules or extrudates; in such cases being it advisable to admix binding materials, such as clay, $SiO_2$, $Al_2O_3$ or other metal oxides to the powder obtained from the synthesis. Prior to the use, zeolites must be at least partially dehydrated, for example by thermal treatment at high temperatures, either under vacuum or not; an activation in air at a temperature ranging from 500° C. to the beginning of the mordenite structural collapse (about 850° C.) is suggested.

The following examples are given to illustrate the present invention, without being however a limitation thereof.

Modalities common to all of the examples

The X-ray analyses were carried out according to the method illustrated in European patent publication 21445.

The infrared spectroscopic analyses were carried out on samples both in the acid and in the sodium form by analyzing the pattern area between 1200 and 200 $cm^{-1}$ with instrument PE 580 (double lattice and resolution of about 1 $cm^{-1}$ in the scanned area). The samples in powder were examined in the form of caesium bromide tablets according to known techniques for zeolites (M. Flanigen; Structural Analysis by IR Spectroscopy A.C.S. 171, 80 (1976) and for $SiO_2$ (T. Rey; UR Absorption $SiO_2$ in Abhang. Ordnung; Z. Krist 123, 263 (1966)).

The $\alpha$-quartz content in the mordenite is determined by weighing, treating the samples in the acid form, after activation at 540° C., with phosphoric acid (at 85% by weight), at a temperature from 200° to 240° C. and for 20–30 minutes according to the Talvitie method (N.A. Talvities; "Determination of Quartz", An. Chem. 23, 623 (1951)).

The content of $Al_2O_3$ and of $Na_2O$ was determined by atomic absorption photometry on the solution obtained by treating the powdered samples with hydrofluoric acid. The $SiO_2$ content is obtained from the datum of calcination at 1200° C. corrected by the content of $Al_2O_3$ and $Na_2O$.

Example 1 (Comparative test)

37.5 g of (DEPP) Br, i.e. diethyl-piperidinium bromide (titre: 99%), 8 g of sodium aluminate (57.2% by weight of $Al_2O_3$, 38.7% by weight of $Na_2O$ and 4.1% by weight of $H_2O$) and 6.4 g of NaOH in drops were dissolved at 60°–70° C. in 236 $cm^3$ of $H_2O$; 88.3 g of an aqueous solution of colloidal silica (Ludox HS) were then added, under strong stirring, while maintaining the same temperature for other 10 minutes. Ludox HS is an aqueous colloidal solution containing 30% by weight of $SiO_2$ besides minimum amounts of NaOH. The molar ratios of the components, expressed as oxides and referred to $Al_2O_3$, and the other characteristic parameters are reported in Table 1.

The gel which formed was transferred into a Hastelloy C autoclave and was heated to 180° C. for 4 days, under stirring and under autogenous pressure. After cooling, the suspension was filtered; the solid product was washed till disappearance of the $Na^+$ ions in the washing liquid, and then dried at 120° C. for 12 hours and activated in air at 540° C. for 10 hours. The product was then treated in a flask, equipped with a reflux cooler, with an aqueous solution of ammonium chloride at 5% by weight; the weight ratio between solution and zeolite was equal to 19.

The flask was heated, under moderate stirring, to 70°–80° C. for 1 hour; the treatment was repeated 4 times on the decanted product by using a fresh solution of NH$_4$Cl.

At the conclusion of the exchange, the product was washed with distilled H$_2$O until disappearance of the Cl$^-$ ions form the washing liquid, and dried at 120° C. for 12 hours.

By activation in air at 540° C. for 10 hours, the acid form or "zeolite H" in powder was obtained. The X-ray diffraction pattern, the IR spectroscopic analysis and the extraction of the acid sample with H$_3$PO$_4$ revealed that the product did not contain α-quartz and consisted substantially of mordenite, the composition of which, on analysis, was the following (% by weight):

SiO$_2$: 85.7%; Al$_2$O$_3$: 13.9% Na$_2$O: 0.4%.

The SiO$_2$/Al$_2$O$_3$ molar ratio in the mordenite was =10.

Example 2 (comparative test)

38.6 g of DEPP-Br, 8.7 g of Na aluminate and 15.8 g of NaOH were dissolved in 460 cm$^3$ of H$_2$O and to the solution there were added, at 60°–70° C., 192.4 g of Ludox HS, whereafter was operated according to example 1; data and results are recorded on Table 1. It should be noted, in particular, the presence of α-quartz (10%) in the final product, besides mordenite at a low SiO$_2$/Al$_2$O$_3$ ratio.

Example 3

77 g of DEPP-Br, 8.7 g of Na aluminate and 8.9 f of NaOH were dissolved in 460 cm$^3$ of H$_2$O at 60°–70° C., whereafter 192 g of Ludox HS were added under intense stirring; then is was operated according to example 1. Data and results are recorded on Table 1, where it is apparent that the product obtained prevailingly consisted of mordenite ME, in which the SiO$_2$:Al$_2$O$_3$ molar ratio was about 20.

EXAMPLE 4

75 g of DEPP-Br were dissolved in 450 cm$^3$ of H$_2$O along with 3 g of Na aluminate and 12 g of NaOH. 205 g of Ludox HS were added to the solution heated to 60°–70° C.; then it was operated as in example 1. Data and results are recorded on Table 1.

It should be noted that the SiO$_2$:Al$_2$O$_3$ molar ratio in the product (30:1) concerns only the mordenite portion of said product, which contained, besides ME mordenite, about 50% by weight of α-quartz.

Example 5

37 g of DEPP-Br, 3 g of Na aluminate and 6.5 g of NaOH were dissolved in 300 cm$^3$ of H$_2$O, 120 g of Ludox HS having been then added to the solution at 60°–70° C.; heating was carried on for further 10 minutes under intense stirring. The molar ratios of the various components, expressed as oxides and referred to Al$_2$O$_3$, are indicated in Table 1.

Figure 2A:
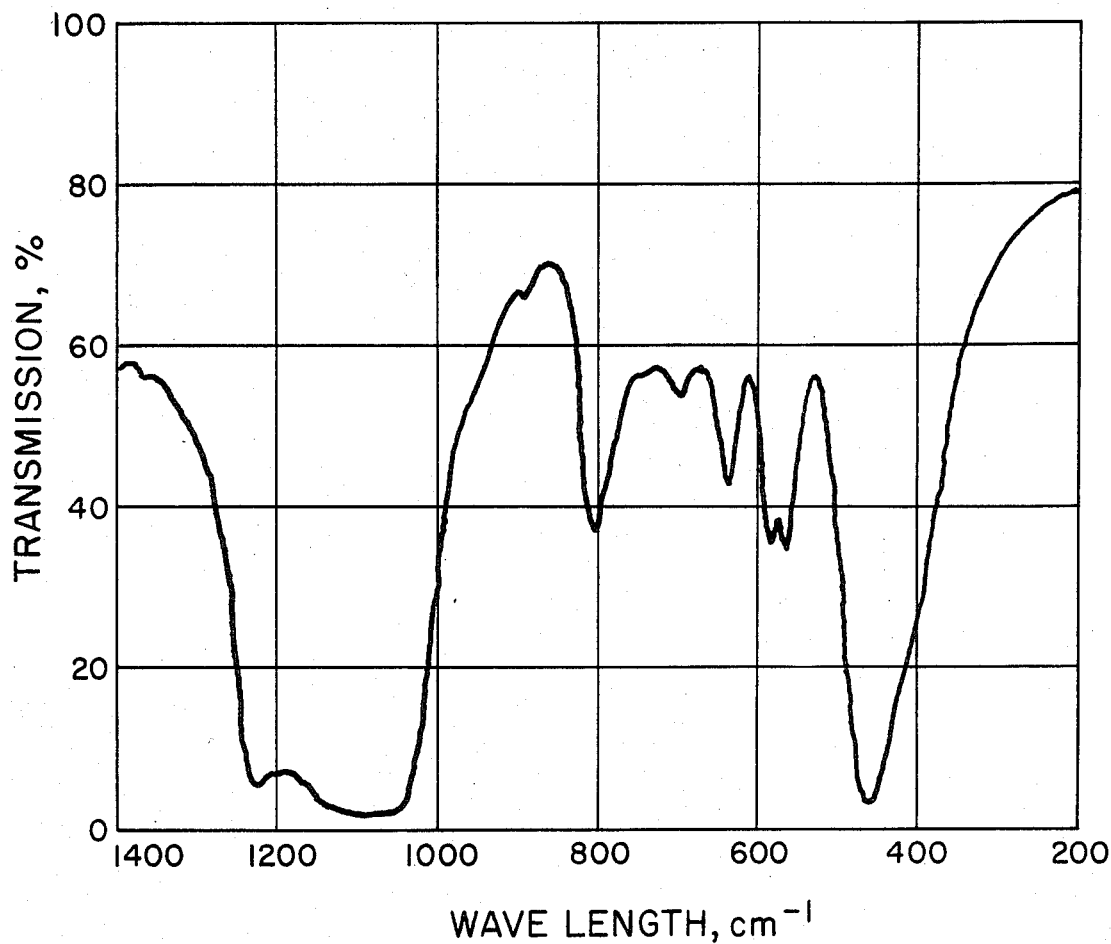
Figure 2B:
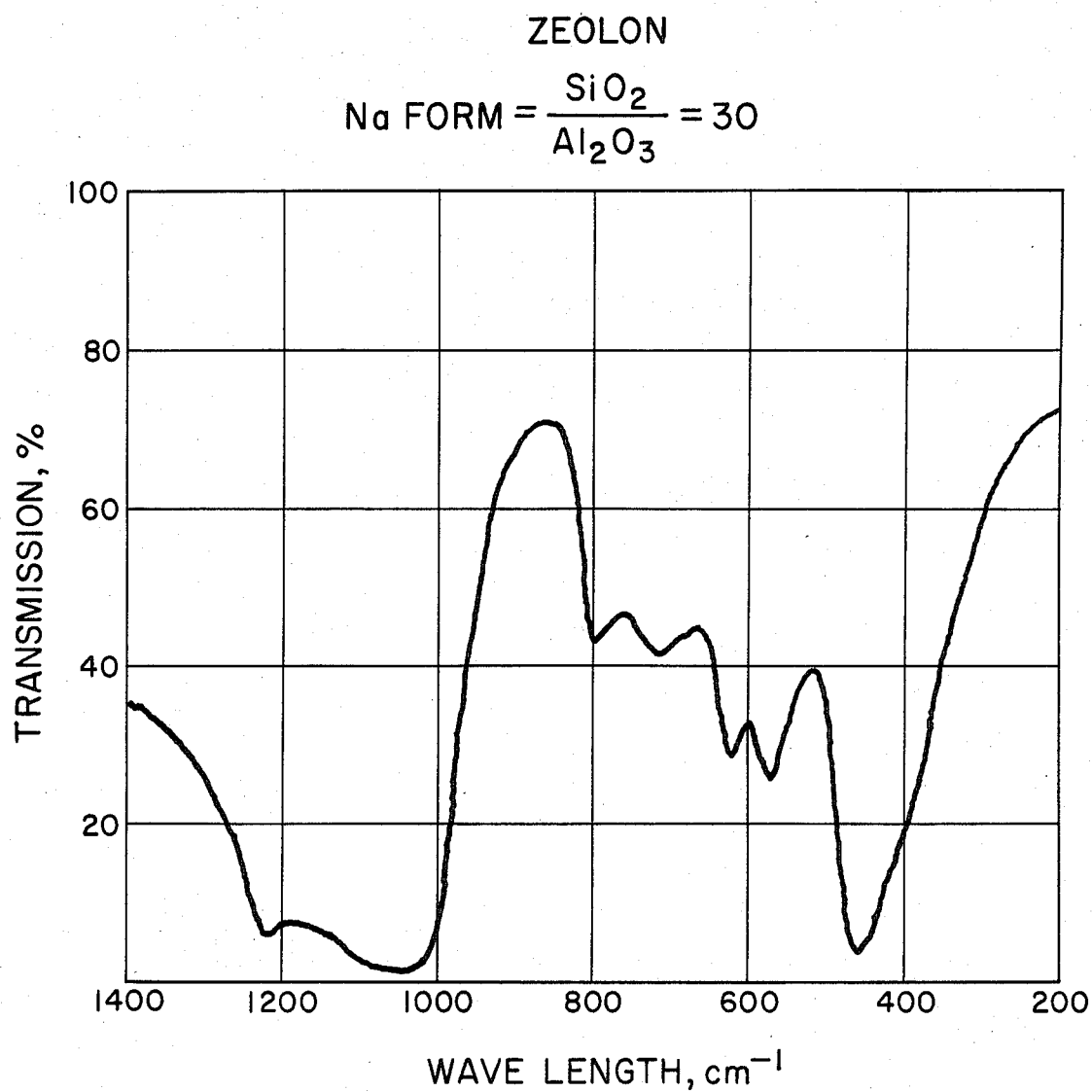

The gel was heated to 160° C. for 6 days under stirring and the crystallized product was treated, according to example 1, till obtaining the acid sample. The X-ray diffraction spectrum, the IR spectrum and the extraction with H$_3$PO$_4$ show that the sample was essentially consisting of ME mordenite (see Table and FIG. 2). The analysis of the product revealed the following composition (% by weight):

SiO$_2$: 94.7%; Al$_2$O$_3$: 5.15%; Na$_2$O: 0.15%.

The SiO$_2$/Al$_2$O$_3$ molar ratio (in the mordenite was =31.

Example 6

22 g of DEPP-Br, 2 g of Na aluminate and 6 g of NaOH were dissolved in 450 cm$^3$ of H$_2$O and the solution was heated to 60°–70° C.; 110 g of Ludox HS were added and it was operated according to example 5, while limiting to 6 days the crystallization time; data and results are indicated in Table 1. The analysis proved that the product is consisting of ME mordenite for the 80% (by weight) and of α-quartz for the 20%.

Example 7

119 g of (DEPP)Br, 3 g of Na aluminate and 4.2 g of NaOH were dissolved in 450 cm$^3$ of H$_2$O and the solution, heated to 60°–70° C., was additioned with 205 g of Ludox HS, then it was operated according to example 1. Data and results are indicated in Table 1. The analysis proved that the product substantially consisted of an amorphous phase, besides minor amounts of ZSM-5 zeolite.

Example 8 (comparative test)

60 g of (DEPP)Br, 5 g of Na aluminate and 8 g of NaOH were dissolved in 500 cm$^3$ of H$_2$O; 220 g of Ludox HS were added, whereafter it was operated as in example 1, but at a higher temperature (190° C.) during crystallization. Data and results are indicated in Table 1. The X-ray diffraction pattern and the IR pattern revealed that the product mainly consisted of MB-28 zeolite.

EXAMPLE 9 (comparative test)

40 g of tetrapropylammonium iodide [(TPA) I], 2.5 g of Na aluminate and 7.5 g of NaOH were dissolved at 80°–90° C. in 380 cm$^3$ of H$_2$O; after having lowered the temperature to 60° C., 225 g of Ludox HS were added. The molar ratios of the components, expressed as oxides and referred to Al$_2$O$_3$, were:

SiO$_2$: 82; Na$_2$O: 7.8; (TPA)$_2$O: 4.6; H$_2$O: 2,100; SP: 0.63.

It was then operated as in example 1, but heating for a longer period of time (5 days) at 180° C.

The X-ray diffraction pattern and the IR pattern revealed that the sample essentially consisted of ZSM-5 zeolite. The analysis revealed the following composition (% b.w.):

SiO$_2$: 97.5%; Al$_2$O$_3$: 1.9%; Na$_2$O: 0.6%.

The SiO$_2$/Al$_2$O$_3$ molar ratio was equal to 70.

Example 10 (comparative test)

The following three solutions were first prepared:

| | |
|---|---|
| (A) Na aluminate (56% of Al$_2$O$_3$, 37% of Na$_2$O) | 2.5 g |
| NaOH | 7.5 g |
| H$_2$O | 50.0 cm$^3$ |
| (B) Tetrabutylammonium iodide [(TBA) I] (titre: 99%) | 25.0 g |
| H$_2$O | 140.0 cm$^3$ |
| (C) Silica sol, type Ludox AS | 225.0 g. |

Ludox AS is an aqueous colloidal solution containing 30.5% by weight of SiO$_2$ and traces of NH$_3$.

Solution A was added to solution B under stirring at 80° C.; then after having lowered the temperature to 60°–70° C. solution C was added. The molar ratios of the components, expressed as oxides and referred to $Al_2O_3$, were as follows:

$SiO_2$: 82; $Na_2O$: 7.8; $(TBA)_2O$: 2.4; $H_2O$: 1,400; SP: 0.76.

The gel was maintained at the same temperature under intense stirring for 10 minutes, whereafter it was changed into an autoclave where it was kept at 160° C. for 2 days under an autogeneous pressure (5–6 atm.) and under stirring.

The product was treated till obtaining the acid sample according to example 1. The X-ray diffraction spectrum revealed that the product was essentially consisting of ZSM-11 zeolite.

REMARKS ON STRUCTURE AND DIFFRACTOGRAMS

ME mordenites exhibit a well-defined crystalline structure in the X-ray diffractogram of the powders; it can be clearly distinguished from the one of already known structures, such as zeolites ZSM-5, 11, 8 etc. (see M. Majer and D. Olson, "Atlas of Zeolites Structures") and, partially, also from the one of synthetic and natural mordenites (having a $SiO_2/Al_2O_3$ ratio equal to 10), all such structures exhibiting pentasilicate subunits. In Table 2 there are indicated the positions of the main DRX reflexes and the respective relative intensities of a typical sample of ME mordenite according to the invention, having a $SiO_2/Al_2O_3$ ratio of about 30, compared with a natural mordenite and with a synthetic mordenite having a $SiO_2/Al_2O_3$ ratio equal to 10. The X-ray diffractogram is reported for the sodic form and for the exchanged and activated form; it is substantially identical, except for slight variations in the intensity of the high-angle reflexes, which are due to the different solvation of the cavities [E. Wu, J. Phys. Chem. 83, 2777 (1979)].

The structures of the samples forming the objects of the examples were recognized as typical of mordenites, making reference to the data of the literature (see, e.g. JCPDS Powder Diffraction File). The presence of more intense reflexes (9.06; 4.51; 3.99; 3.47; 3.22), at well known positions of the natural and synthetic mordenites, confirm that they belong to this class.

The IR-spectroscopic analysis of ME mordenites, with respect to synthetic mordenites with a $SiO_2/Al_2O_3$ ratio = 10 (see FIG. 2), shows significant differences in the area from 500 to 900 $cm^{-1}$, which are ascribable to the different composition $(Al_2O_3/SiO_2)$ of the silicate structure; see B. Hyon Ha et al., J. Chem. Soc., Faraday Trans. Vol. 75, 1245 (1979).

In several preparations reported in the examples, the phase system is complicated by the presence of other crystalline phases, in particular by crystalline silica of the $\alpha$-quartz type, easily recognizable, on analysis under the optical microscope, from the IR spectrum and from the presence, in the X-ray diffractogram of the powders, of the specific reflexes of the $\alpha$-quartz (4.26; 3.34; 1.82).

CATALYTIC ACTIVITY TESTS

Example A (Toluene disproportioning)

30 parts by weight of acid zeolite, activated at 540° C. for 10 hours, were homogeneously mixed with 3 parts by weight of bentonite and kneaded with a proper amount of $H_2O$. By extrusion of the resulting mass, small cylinders having a 1 mm diameter were obtained; the extrudates were dried 12 hours at 110°–120° C. and activated at 540° C. for 2 hours. 30 $cm^3$ of the catalyst so obtained (apparent volume) were introduced into a steel reactor having an inside diameter of 16 mm and electrically heated; conditions and results of the toluene disproportioning reaction are recorded on Table 3. As is apparent, the ME zeolite having a high $SiO_2:Al_2O_3$ ratio, obtained through the process according to the invention, are much more active not only than the conventional mordenites, but also than other zeolites of different structure.

Example B (Isomerization of xylenes)

30 $cm^3$ of a catalyst prepared according to example A were introduced into the reactor described in example A; the reaction conditions and results are indicated in Table 4. As is apparent, the ME mordenitic zeolites having a high $SiO_2:Al_2O_3$ ratio are much more active not only than the conventional mordenites, but also than the zeolites of ZSM-5 and MB-28 type, which are the best ones in this field; the latter, although they are endowed with a higher selectivity in ortho- and paraxylene, exhibit lower yields than ME mordenites of examples 5 and 6.

TABLE 1

| Parameters | Ex. 1* | Ex. 2* | Ex. 3 | Ex. 4 | Ex. 5 | Ex. 6 | Ex.7* | Ex. 8* |
|---|---|---|---|---|---|---|---|---|
| (1) Initial molar ratios: | | | | | | | | |
| $SiO_2Al_2O_3$ | 10 | 20 | 20 | 62 | 36.3 | 49.9 | 62 | 40 |
| $Na_2O/Al_2O_3$ | 2.9 | 5.2 | 3.4 | 10 | 6.0 | 7.8 | 4.2 | 4.7 |
| $(DEPP)_2O/Al_2O_3$ | 1.9 | 1.8 | 3.6 | 10 | 5.0 | 4.4 | 15.2 | 4.8 |
| $H_2O/Al_2O_3$ | 370 | 680 | 680 | 2000 | 1300 | 2100 | 2000 | 1300 |
| $H_2O/SiO_2$ | 37 | 34 | 34 | 32.26 | 35.81 | 42.08 | 32.26 | 32.50 |
| (2) Total cationic dilution: | | | | | | | | |
| $r = H_2O/[Na_2O + (DEPP)_2O]$ | 77 | 97 | 97 | 100 | 118 | 172 | 103 | 137 |
| (3) SP = $Na_2O/[Na_2O + (DEPP)_2O]$ | 0.6 | 0.75 | 0.5 | 0.5 | 0.55 | 0.64 | 0.2 | 0.5 |
| (4) $SiO_2$ amount, referred to the initial total $SiO_2$ which is transferred into ME mordenite | — | 60% | 90% | 40% | 80% | 70% | — | — |
| (5) Final composition: | | | | | | | | |
| $SiO_2Al_2O_3$ (molar) | ~10** | ~13** | ~20** | ~30** | ~31** | ~39** | 69 | 57 |
| $\alpha$-quartz (% by weight) | — | ~10 | ~8 | ~50 | — | ~20 | (a) | (b) |
| total $SiO_2$ (% by weight) | 85.7 | 89.9 | 93.0 | 97.3 | 94.7 | 96.4 | 97.5 | 96.9 |
| $Al_2O_3$ (% by weight) | 13.9 | 10.1 | 7.0 | 2.5 | 5.15 | 3.3 | 2.40 | 2.90 |
| $Na_2O$ (% by weight) | 0.4 | traces | traces | 0.2 | 0.15 | 0.3 | 0.15 | 0.2 |
| (6) Crystallization temperature and time | 180° C. for | As for | As for | As for | 160° C. for | 160° C. for | As for | 190° C. for |

TABLE 1-continued

| Parameters | Ex. 1* | Ex. 2* | Ex. 3 | Ex. 4 | Ex. 5 | Ex. 6 | Ex.7* | Ex. 8* |
|---|---|---|---|---|---|---|---|---|
| | 4 days | ex. 1 | ex. 1 | ex. 1 | 6 days | 5 days | ex. 1 | 4 days |

*Comparative test
**Final $SiO_2:Al_2O_3$ molar ratio in mordenite only, alpha-quartz excluded.
(a) Amorphous $SiO_2$ + traces of ZSM5
(b) MB28

TABLE 2

| ME zeolite obtained according to example 5 $SiO_2:Al_2O_3 = 31$ Na Form | | Commercial synthetic mordenite Zeolon H 900 (1) $SiO_2:Al_2O_3 = 10$ H Form | | | Natural mordenite (Ptylolite) (2) $SiO_2:Al_2O_3 = 10$ Na Form | |
|---|---|---|---|---|---|---|
| d | $1/l_o \times 100$ | H form | d | $1/l_o \times 100$ | d | $1/l_o \times 100$ |
| 13.51 | 20 | Practical- | 13.60 | 20 | 13.70 | 50 |
| — | — | tical- | — | — | — | — |
| 10.10 | — | ly co- | 10.16 | 20 | — | — |
| 9.06 | 80 | inci- | 9.03 | 80 | 9.10 | 90 |
| 6.55 | 80 | dent | 6.54 | 40 | 6.61 | 90 |
| — | — | with | 6.37 | 10 | 6.38 | 40 |
| 6.02 | — | Na | 6.05 | 10 | 6.10 | 50 |
| 5.76 | — | form | 5.75 | 20 | 5.79 | 50 |
| 4.51 | 50 | | 4.51 | 40 | — | — |
| 3.97 | 80 | | 3.99 | 75 | 4.00 | 90 |
| 3.82 | 20 | | 3.82 | 10 | 3.84 | 60 |
| 3.74 | 20 | | 3.76 | 15 | 3.76 | 20 |
| 3.46 | 100 | | 3.47 | 100 | 3.48 | 100 |
| 3.34 | — | | 3.37 | 50 | 3.39 | 90 |
| 3.20 | 80 | | 3.22 | 30 | 3.22 | 100 |
| 2.87 | 20 | | — | — | — | — |

(1) The diffractogram of Zeolon H is substantially identical with the one reported by D. W. Breck (Zeolite table 4.68 Wiley 974) and by D. Domine (Synthes. Mordenite - S.C.I. 968); the zeolite obtained according to example 1 has a diffractogram identical with that of the Table.
(2) The cited data are taken from JCPDS File 6-0239.

TABLE 3

| CATALYST | CRYSTALLINE PHASES | $SiO_2^*/Al_2O_3$ | LHSV** $(H^{-1})$ | TEMP. (°C.) | CONV. OF TOL. | % BY WEIGHT OF THE PRODUCTS | | | | | |
|---|---|---|---|---|---|---|---|---|---|---|---|
| | | | | | | TOL. | BENZ. | XYL. | ETB. | LIGHT | HEAVY |
| H-900*** | Mordenite | 10 | 2.1 | 350 | 16.4 | 83.6 | 5.6 | 7.5 | 0.1 | 3.1 | 0.1 |
| | | | 2.1 | 400 | 32.2 | 67.7 | 10.5 | 10.4 | 0.3 | 7.0 | 4.1 |
| Ex. 5 | ME mordenite | 31 | 1.9 | 350 | 52.5 | 47.5 | 21.9 | 24.0 | 0.6 | 3.1 | 2.9 |
| | | | 1.9 | 400 | 58.5 | 41.5 | 22.1 | 23.0 | 1.2 | 6.8 | 5.4 |
| Ex. 6 | ME mordenite + + α-quartz (10%) | 39 | 2.6 | 350 | 43.0 | 57.0 | 17.2 | 19.6 | 0.4 | 4.0 | 1.8 |
| | | | 2.4 | 400 | 52.1 | 47.9 | 21.8 | 23.5 | 0.5 | 1.7 | 4.4 |
| Ex. 8 | MB-28 | 57 | 2.3 | 350 | 9.3 | 90.7 | 3.0 | 4.1 | — | 2.1 | 0.1 |
| | | | 2.2 | 400 | 26.3 | 73.7 | 9.7 | 12.4 | — | 4.0 | 0.2 |
| Ex. 9 | ZSM-5 | 70 | 2.6 | 350 | 3.6 | 96.4 | 1.0 | 1.2 | — | 0.9 | 0.5 |
| | | | 2.3 | 400 | 14.4 | 85.6 | 4.3 | 5.4 | — | 4.4 | 0.3 |
| Ex. 19 | ZSM-11 | 70 | 2.3 | 350 | 6.6 | 93.4 | 1.0 | 1.1 | — | 4.3 | 0.2 |
| | | | 2.3 | 400 | 12.7 | 87.3 | 4.0 | 5.1 | — | 3.4 | 0.2 |

Note:
Feed: Toluene + $H_2$; $H_2$/toluene molar ratio: 6.5; pressure: 40 atm.; the tests with H-900 and with the zeolites as per examples 8, 9 and 10 were carried out for comparative purposes.
*Molar ratio in the prevailing phase(ME mordenite for examples 5 and 6).
**Space velocity calculated on the activated crystalline phase.
***Commercial product by Norton.

TABLE 4

| CATALYST | CRYSTALLINE PHASES | $SiO_2/Al_2O_3$ | LHSV** $(h^{-1})$ | CONV. OF M-XYL. | % BY WEIGHT OF THE PRODUCTS | | | | | |
|---|---|---|---|---|---|---|---|---|---|---|
| | | | | | XYLENES | | | BENZ. | TOL. | HEAVY |
| | | | | | META | PARA | ORTHO | | | |
| H-900 | Mordenite | 10 | 6.0 | 26.7 | 73.2 | 10.6 | 10.6 | 0.1 | 1.8 | 1.8 |
| Ex. 1 | Mordenite | 10 | 6.7 | 4.0 | 95.8 | 2.1 | 1.6 | — | 0.5 | traces |
| Ex. 2 | Mordenite + + 10% α-quartz | 13* | 7.4 | 2.7 | 97.1 | 1.5 | 1.2 | — | 0.2 | traces |
| Ex. 3 | ME mordenite + + 8% α-quartz | 20* | 7.4 | 28.3 | 71.5 | 14.0 | 11.4 | traces | 1.5 | 1.6 |
| Ex. 4 | ME mordenite + + 50% α-quartz | 30* | 13.3 | 30.9 | 68.9 | 15.3 | 13.1 | traces | 1.3 | 1.3 |
| Ex. 5 | ME mordenite | 31 | 6.7 | 63.5 | 36.3 | 16.7 | 14.7 | 0.4 | 11.7 | 20.1 |
| Ex. 6 | ME mordenite + + 20% α-quartz | 39* | 8.3 | 62.8 | 37.0 | 16.3 | 14.4 | 0.5 | 11.9 | 19.9 |
| Ex. 8 | MB-28 | 57 | 6.7 | 46.2 | 53.7 | 23.3 | 21.5 | — | 0.8 | 0.7 |
| Ex. 9 | ZSM-5 | 70 | 6.7 | 39.9 | 60.0 | 23.4 | 16.5 | — | 0.1 | traces |
| Ex. 10 | ZSM-11 | 70 | 6.7 | 44.8 | 55.1 | 23.6 | 20.6 | — | 0.5 | 0.3 |

Note:
Feed: $H_2$ + meta-xylene; $H_2$/meta-xylene molar ratio = 5; pressure: 15 atm.; temperature: 300° C.
*Molar ratio in the mordenite
**Space velocity calculated on the activated crystalline phase
***Light products present in the traces.

What is claimed is:

1. A process for synthesizing mordenites having a high catalytic activity, in which the $SiO_2:Al_2O_3$ molar ratio is in the range 16 to 40, said process comprising the steps of mixing an organic base with $H_2O$ and at least a Na compound, an Al compound, and a Si compound, and being characterized in that said base is (DEPP)+OH− or a salt thereof, that the crystallization temperature is from 140° C. to 160° C. and both it and the SP factor are selected within the area of AEFD of FIG. 1 of the drawing, the crystallization time being longer than 2 days, and in that the following molar ratios between the abovesaid compounds, expressed as oxides, are employed:

$Na_2O:Al_2O_3 = 1$ to 10; $(DEPP)_2O:Al_2O_3 = 1$ to 15; $SiO_2:Al_2O_3 = 20$ to 70; $H_2O:Al_2O_3 = 500$ to 3,000; $H_2O:SiO_2 = 25$ to 45.

2. The process according to claim 1, characterized in that the molar ratios are in the following ranges:

$Na_2O:Al_2O_3 = 2$ to 8; $(DEPP)_2O:Al_2O_3 = 2$ to 10; $SiO_2:Al_2O_3 = 20$ to 50; $H_2O:Al_2O_3 = 500$ to 3,000; $H_2O:SiO_2 = 35$ to 45.

3. The process according to claim 1, in which the crystallization time is from 4 to 6 days.

4. The process according to claim 1, characterized in that the salt is (DEPP)Br, the Na compound is NaOH, the Al compound is Na aluminate, and the Si compound is a silica sol.

5. A process for preparing a catalyst for the disproportioning of toluene, containing a mordenite having a $SiO_2:Al_2O_3$ molar ratio from 16 to 40, said process comprising the steps of mixing an organic base with $H_2O$ and at least a Na compound, an Al compound, and a Si compound, and being characterized in that said base is (DEPP)+OH− or a salt thereof, in that the mixture is crystallized at a temperature from 140° C. to 160° C., in that both said temperature and the SP factor are selected within the area AEFD of FIG. 1 of the drawing, the crystallization time being longer than two days, and in that the following molar ratios between the abovesaid compounds, expressed as oxides, are employed: $Na_2O:Al_2O_3 = 1$–10; $(DEPP)_2O:Al_2O_3 = 1$–15; $SiO_2:Al_2O_3 = 20$–70; $H_2O:Al_2O_3 = 500$–3,000; $H_2O:SiO_2 = 25$–45; thereafter filtering the crystallization mixture, drying it in an oven for 10–12 hours at 120° C. and activating it in air for 2–10 hours at between 400° C. and 600° C.

6. The process according to claim 5, characterized in that said mordenite is prepared in the acid form by exchange with $NH_4Cl$ and successive calcining between 300° C. and 650° C., the zeolite powder so exchanged being then kneaded with 10–50% by weight of another binding material and being extruded in preselected form, the extruded mixture being heated, dried and activated by treatment in air at high temperature of 500° C. to the beginning of mordenite structural collapse.

7. The process according to claim 6, in which the binding material is selected from the group consisting of clay, $SiO_2$ and $Al_2O_3$.

8. The process according to claim 6, in which the calcining is performed at a temperature of 400° to 550° C.

* * * * *